(12) United States Patent
Olsen et al.

(10) Patent No.: US 9,044,250 B2
(45) Date of Patent: Jun. 2, 2015

(54) BONE TREATMENT SYSTEM

(76) Inventors: Russell G. Olsen, Cedar City, UT (US); Steven S. Ramboz, Summit, UT (US)

(*) Notice: Subject to any disclaimer, the term of this patent is extended or adjusted under 35 U.S.C. 154(b) by 197 days.

(21) Appl. No.: 13/599,938

(22) Filed: Aug. 30, 2012

(65) Prior Publication Data
US 2013/0231668 A1  Sep. 5, 2013

Related U.S. Application Data

(60) Provisional application No. 61/529,171, filed on Aug. 30, 2011.

(51) Int. Cl.
*A61F 5/00* (2006.01)
*A61B 17/16* (2006.01)
*A61B 17/17* (2006.01)
*A61B 17/15* (2006.01)

(52) U.S. Cl.
CPC .......... *A61B 17/16* (2013.01); *A61B 17/17* (2013.01); *A61B 17/151* (2013.01); *A61B 17/1739* (2013.01); *A61B 2017/1775* (2013.01)

(58) Field of Classification Search
CPC .............................. A61B 17/152; A61B 17/151
USPC ....................................................... 606/87, 88
See application file for complete search history.

(56) References Cited

U.S. PATENT DOCUMENTS

| 6,796,986 B2 * | 9/2004 | Duffner | 606/87 |
| 2007/0265634 A1 * | 11/2007 | Weinstein | 606/87 |

* cited by examiner

*Primary Examiner* — Andrew Yang
(74) *Attorney, Agent, or Firm* — Kunzler Law Group, PC

(57) ABSTRACT

A system for removing bone growths and realigning bones includes a bone planer and an osteotomy guide. The bone planer includes a hollow sleeve that has an end embeddable within a bone. The bone planer also includes a rotary blade that is coupled to the hollow sleeve. The rotary blade is positioned within and rotatable relative to the hollow sleeve. The osteotomy guide includes a distal portion and a proximal portion. The distal and proximal portions are slidably coupled together. Each of the distal and proximal portions includes an upright that defines a cut guide surface. A space defined between the cut guide surfaces defines a cut path corresponding with a desired cut through the bone.

7 Claims, 8 Drawing Sheets

BONE TREATMENT SYSTEM

CROSS-REFERENCE TO RELATED APPLICATION

This application claims the benefit of U.S. Provisional Patent Application No. 61/529,171, filed Aug. 30, 2011, which is incorporated herein by reference.

FIELD

The present disclosure relates generally to a system for treating bones, and more specifically to a bone treatment system for removing bone growths and realigning bones.

BACKGROUND

The removal of bone abnormalities, such as bunions, is a common surgical procedure. With nearly all surgical techniques, simplicity and accuracy of the procedure and minimization of non-aesthetically pleasing scarring are desired. However, conventional bone abnormality removal procedures, such as various planing techniques, are very complex and typically leave large, unpleasant scars.

For example, conventional planing techniques require the overlaying tissue to be folded back and secured prior to planing the bone. Such techniques enhance the complexity of the procedure and result in large incisions, which lead to large scars and longer, more painful recovery.

Following the removal of bone abnormalities from a bone, commonly the bone is at least slightly deformed or misaligned. Accordingly, bone alignment procedures may be necessary to correct such deformities or misalignment. Conventional procedures for aligning bones require an osteotomy of cutting of the bone into two segments, moving one bone segment into a more proper alignment with the other bone segment, and fixating the moved bone segment relative to the other bone segment for a period of time to induce tissue growth between and reattachment of the aligned segments. Although conventional osteotomy procedures for correcting misaligned bones are common, they suffer from several shortcomings. For example, maintaining the relative rotational position of the bone segments while moving the segments into alignment is particularly difficult. Conventional procedures are prone to allowing such relative rotation of the bone segments during the moving step. Also, most conventional osteotomy and realignment procedures do not provide an accurate and reliable method for fixating the bone segments once moved into alignment.

SUMMARY

The subject matter of the present application has been developed in response to the present state of the art, and in particular, in response to the problems and needs in the bone abnormality and realignment art that have not yet been fully solved by currently available techniques and devices. Accordingly, the subject matter of the present application has been developed to provide apparatus, systems, and methods for removing bone abnormalities and realigning bones that overcomes at least some shortcomings of the prior art.

According to one embodiment, a system for removing bone growths and realigning bones includes a bone planer and an osteotomy guide. The bone planer includes a hollow sleeve that has an end embeddable within a bone. The bone planer also includes a rotary blade that is coupled to the hollow sleeve. The rotary blade is positioned within and rotatable relative to the hollow sleeve. The osteotomy guide includes a distal portion and a proximal portion. The distal and proximal portions are slidably coupled together. Each of the distal and proximal portions includes an upright that defines a cut guide surface. A space defined between the cut guide surfaces defines a cut path corresponding with a desired cut through the bone.

In some implementations, the system also includes a primary guide wire embeddable within the bone growth. The bone planer includes an interior channel that is slidably engageable with the primary guide wire. Engagement between the primary guide wire and the interior channel maintains the orientation of the bone planer relative to the bone. The proximal portion includes an aperture that is engageable with the primary guide wire. Engagement between the primary guide wire and the aperture maintains a position of the proximal portion relative to the bone.

In another embodiment, a bone planer includes a hollow sleeve that has an end fixedly embeddable within a bone. The bone planer also includes a rotary blade that is rotatably coupled to the hollow sleeve and positioned within the hollow sleeve. In some implementations, the rotatory blade has a head and a plurality of blades coupled to the head. The sleeve can include a plurality of debris ports and/or an injection port that is coupleable to a material source. An end of the hollow sleeve that is fixedly embeddable within a bone may include anchors.

In some implementations of the bone planer, the rotary blade is coupled to an end of a rotatable shaft at least partially positionable within the hollow sleeve. The rotatable shaft can have a hollow interior channel. The rotary blade can be positioned between a first open end of the hollow sleeve and a second end of the hollow sleeve opposing the first open end.

In certain implementations, the rotary blade is translationally movable within the hollow sleeve in a direction parallel to a central axis of the hollow sleeve. The bone planer can also have a biasing element that is positionable within the hollow sleeve and engageable with the rotary blade to bias the rotary blade away from the end of the hollow sleeve that is fixedly embeddable within a bone.

According to yet another embodiment, an osteotomy guide includes a distal portion that has a first upright defining a first cut guide surface, and a proximal portion that has a second upright defining a second cut guide surface. The distal portion is slidably coupleable to the proximal portion. When the distal portion is slidably coupled to the proximal portion, a cut path for receiving a cutting blade is defined between the first and second cut guide surfaces. The cut path can have a V-shape.

In some implementations of the osteotomy guide, the distal portion includes at least one aperture for receiving a guide wire, and the proximal portion includes at least one aperture for receiving a guide wire. According to yet some implementations, the proximal portion includes at least a portion of a joystick accessible by a user to slide the proximal portion relative to the distal portion. In certain implementations, the proximal portion includes first and second sections. The first section can be axially fixedly coupled to the distal portion and the second section can be axially movable relative to the distal portion. The second upright is fixedly attached to the second section.

In yet some implementations of the osteotomy guide, the distal portion is slidably coupleable to the proximal portion via a coupling mechanism. When slidably coupling the distal and proximal portions, the coupling mechanism allows movement of the distal portion relative to the proximal portion in a first direction and prevents movement of the distal portion relative to the proximal portion in a second direction perpendicular to the first direction.

According to some implementations, the osteotomy guide also includes at least one distal panel that is removably coupleable to the distal portion. The osteotomy guide may also include a proximal panel that is removabaly coupleable to the proximal portion. The distal panel can be pivotable relative to the distal portion and the proximal panel can be pivotable relative to the proximal portion. The distal panel may include at least one guide sleeve or a guide wire aperture, and the proximal panel may include at least one guide sleeve or a guide wire aperture.

In one embodiment, a method for removing bone growths includes forming an opening in tissue overlaying a bone, and positioning a hollow sleeve within the opening. The hollow sleeve includes a rotary blade that is rotatably coupled to the hollow sleeve and positioned within the hollow sleeve. The method further includes embedding an end of the hollow sleeve within the bone such that the hollow sleeve prevents the tissue overlaying the bone from penetrating an interior of the hollow sleeve. Further, the method includes rotating the rotary blade relative to the hollow sleeve and positioning the rotating rotary blade into contact with the bone to planarize the bone.

In another embodiment, a method for cutting and aligning bone includes securing a proximal portion of an osteotomy guide to a bone to be cut where the proximal portion defines a first cut guide surface. The method also includes slidably coupling a distal portion of the osteotomy guide to the proximal portion where the distal portion defines a second cut guide surface. When the distal portion is slidably coupled to the proximal portion, a cut path is defined between the first and second cut guide surfaces. The method further includes passing a cutting blade through the cut path and into the bone to cut the bone into a first segment and second segment. Additionally, the method includes slidably moving the proximal portion relative to the distal portion to move the first segment of the bone into a new position relative to the second segment of the bone. Finally, the method includes fixing the first segment of the bone in the new position relative to the second segment of the bone.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE FIGURES

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which.

DETAILED DESCRIPTION

Figure 1:
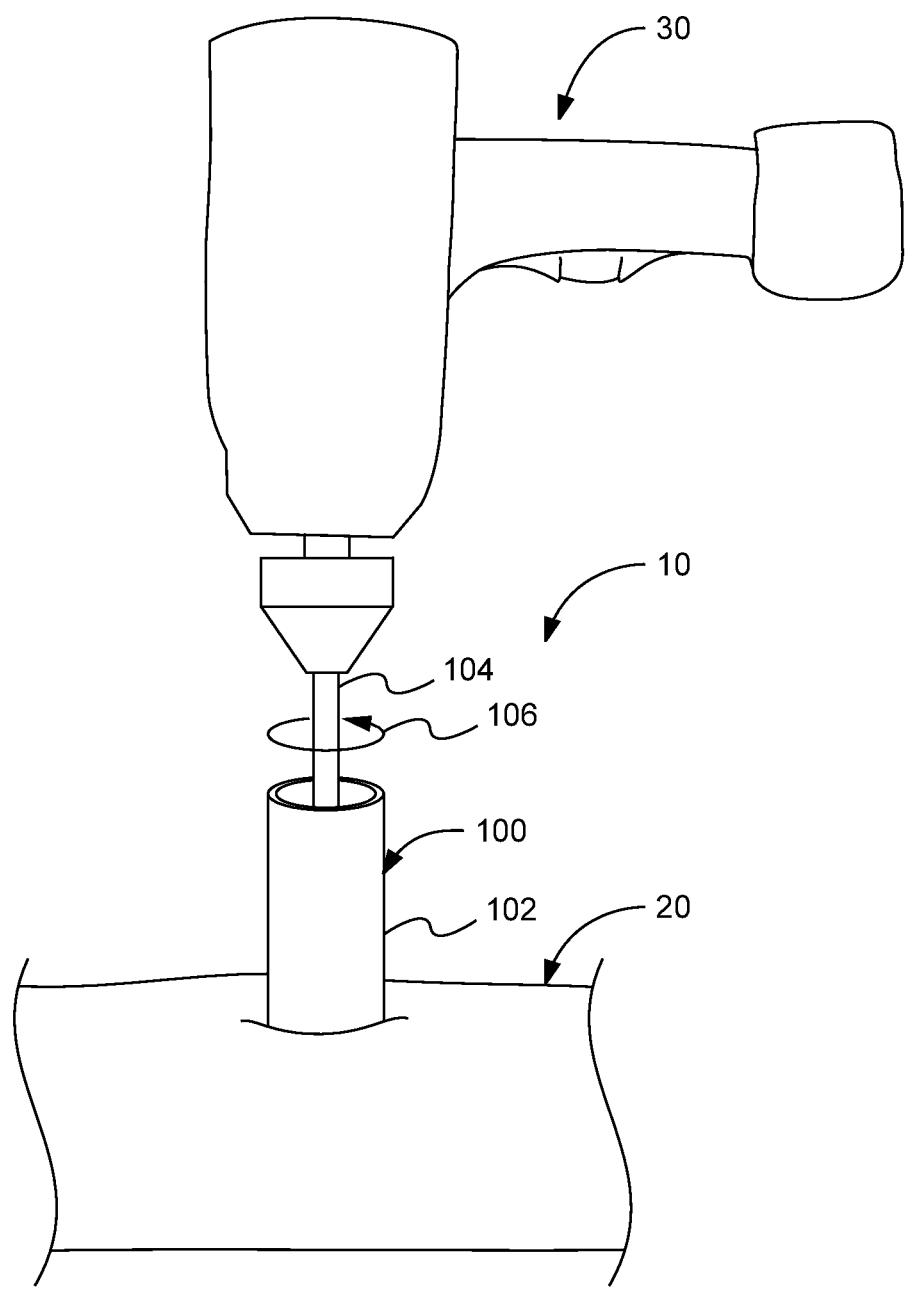
FIG. 1 is a side view of a bone planer in the process of removing a bone abnormality from a bone layer of tissue according to one embodiment.
Figure 3:
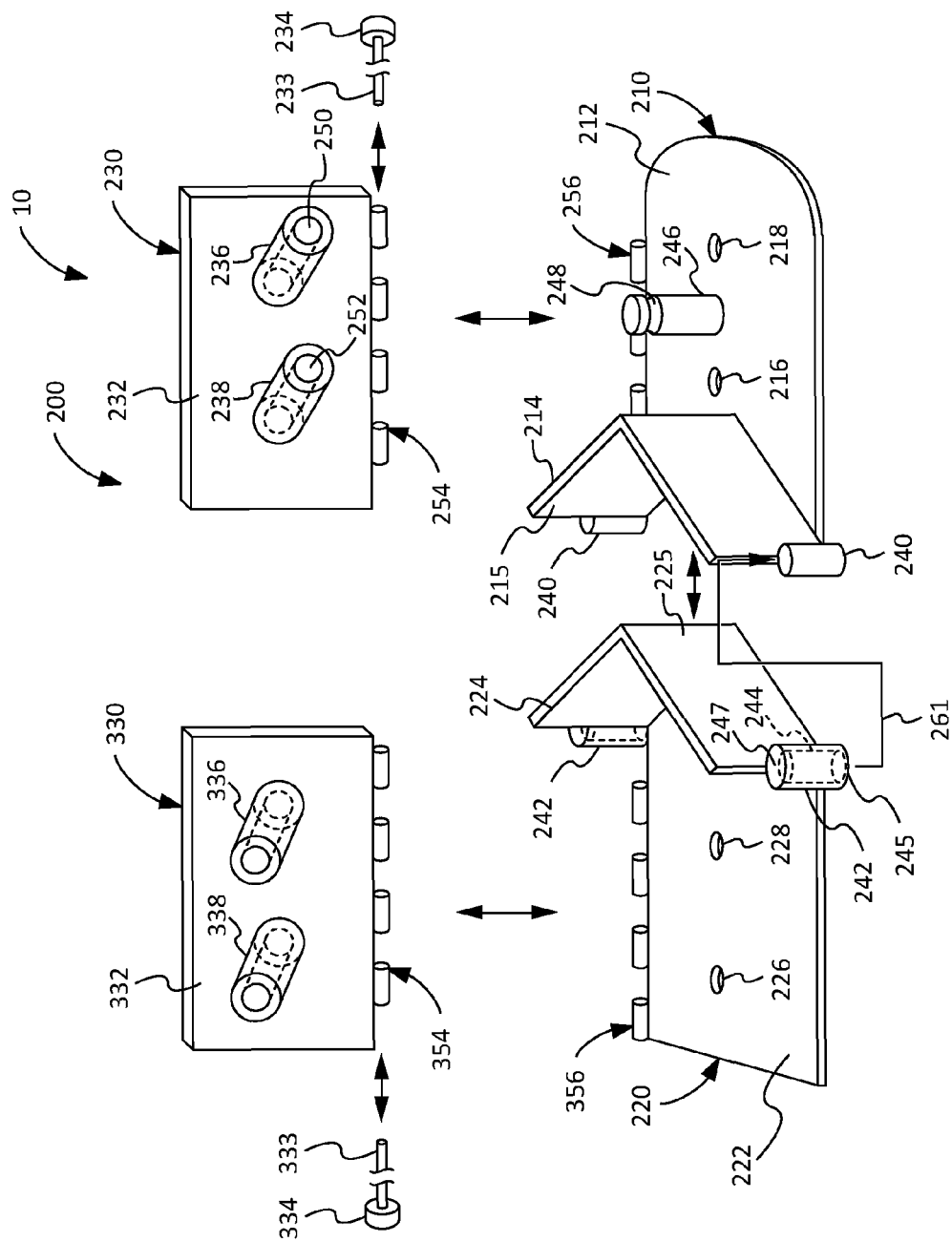
FIG. 3 is an exploded perspective view of an osteotomy guide according to one embodiment.

As discussed above, a need exists for an improved system, and associated apparatus and method, for treating abnormalities (e.g., spurs and bunions) in bones. Beneficially, such a system, apparatus, and method would improve the current shortcomings associated with conventional techniques for removing bone growths and/or realigning bones. Referring to FIGS. 1 and 3, a system 10 for removing bone growths and realigning bones includes a bone planer 100 and an osteotomy guide 200.

Figure 2:
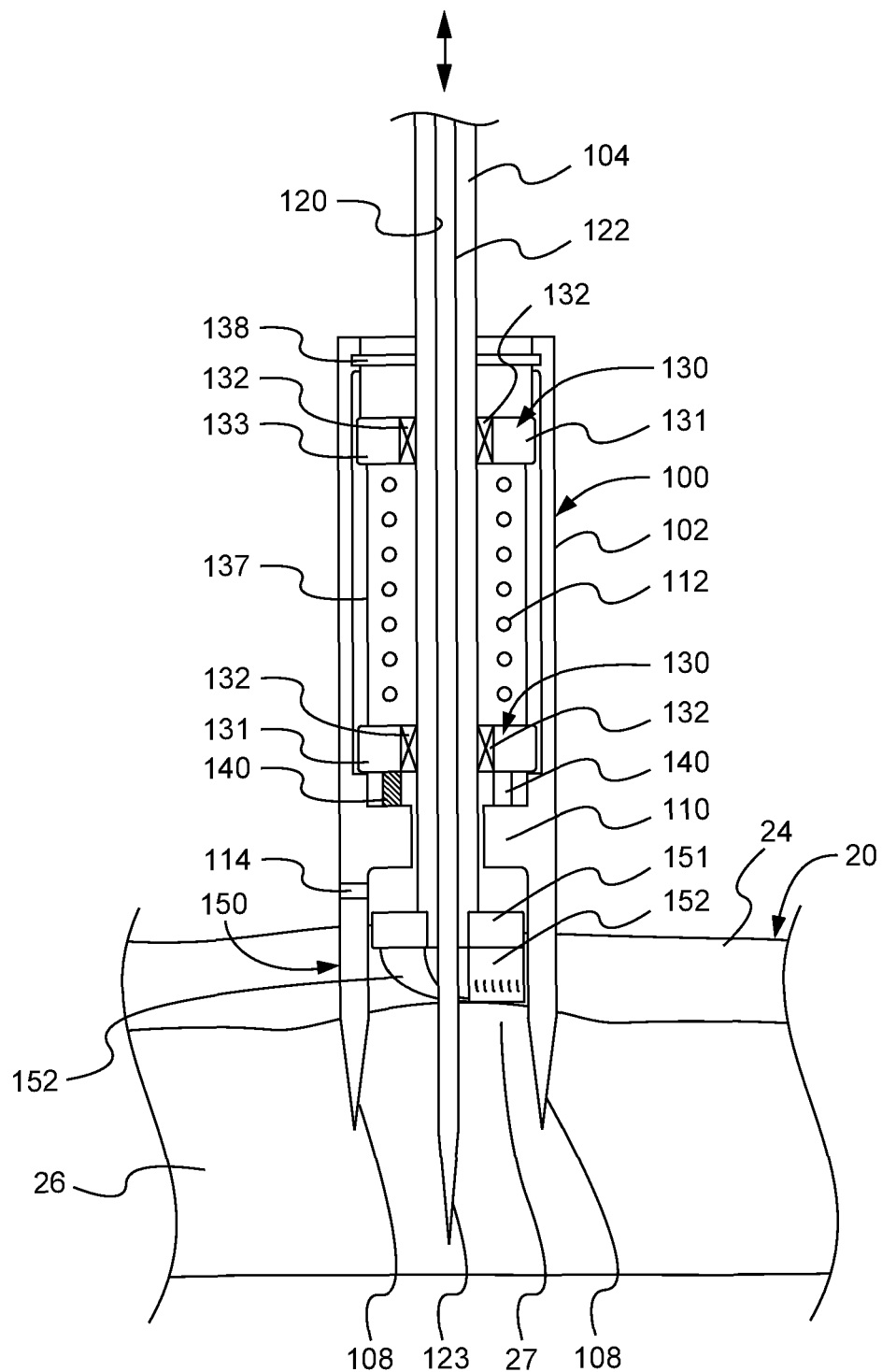
FIG. 2 is a cross-sectional side view of the bone planer of FIG. 1.

As shown in FIGS. 1 and 2, the bone planer 100 includes a stationary sleeve 102 within which a series of blades 152 (see, e.g., FIG. 2) are rotated as indicated by directional arrows 106. The blades 152 are coupled to a cannulated shaft 104, which is rotated via a drill 30 or other similar driving device. Accordingly, the drill 30 rotatably drives the blades 152 via the cannulated shaft 104, which is releasably coupled to the drill. While rotating, the blades 152 are positioned into contact with a portion of bone to plane (e.g., incrementally remove layers of) the bone. As the blades rotate and remove bone, the sleeve 102 acts to prevent the overlaying tissue from coming into contact with the blades. Conventional planing techniques require the overlaying tissue to be folded back and secured prior to planing the bone. Because the sleeve 102 is at least partially embedded within the overlaying tissue, and prevents the tissue from contacting the blades, the overlaying tissue does not need to be folded back and secured. In other words, the system 10 with the protective sleeve 102 facilitates the use of a smaller incision and fewer steps for planning bone compared to previous techniques.

As shown in FIG. 2, the sleeve 102 is substantially tubular shaped to define a hollow interior. The sleeve 102 includes anchors 108 positioned proximate a distal end of the sleeve. The anchors 108 are embeddable into a bone layer 26 of the tissue 20. In certain implementations, the anchors 108 define a circular-shaped serrated edge with a plurality of teeth. In such implementations, the anchors 108 are embedded into the bone layer 26 by rotating the serrated edge to effectively saw into the bone layer. In alternative implementations, the anchors 108 include a plurality of sharp stakes positioned about a distal end of the sleeve 102. With the anchors 108 embedded into the bone layer 26, rotation of the sleeve 102 relative to the bone layer is prevented. Additionally, with the anchors 108 embedded into the bone layer 26, the wall of the sleeve 102 extending transversely away from the bone layer blocks the overlaying tissue 24 from entering into the interior of the sleeve.

The cannulated shaft 104 is positioned coaxially within the sleeve 102 and extends a substantial length of the sleeve. The cannulated shaft 104 is configured to rotate relative to the sleeve 102 while being maintained is a coaxial position within the sleeve. To facilitate relative rotation and maintain coaxial alignment with the sleeve 102, the bone planer 100 includes at least one coupling mechanism 130. The coupling mechanism 130 can be any of various mechanisms or combinations. In the illustrated embodiment, the coupling mechanism 130 includes a ring 131 with at least one tab 133 that extends into a notch or channel 137 formed in the sleeve 102. Engagement between the tab 133 and the channel prevents relative rotation of the ring 131 and the sleeve 102. A bearing 132 (e.g., a ball bearing) is positioned within the ring 131 between the shaft 104 and the ring. The shaft 104 sleeve 102 can be press-fit within the bearing 132 such that the shaft 104 does not move translationally relative to the bearing. In this manner, the shaft 104 is held in a coaxial arrangement relative to the sleeve 102, but is allowed to rotate relative to the sleeve.

In some embodiments, the planer 100 is self-retractable. For example, the channel 137 formed in the sleeve 102 can extend longitudinally along an interior surface of the sleeve in a direction parallel to the axis of the sleeve. Accordingly, the coupling mechanism 130 allows translational movement of the ring 131, and thus the cannulated shaft 104, in a direction parallel to the central axis of the sleeve 102 as the tab 133 slides along the channel. A shelf 110 may be formed on an interior surface of the sleeve 102. The planer 100 further includes at least one spring 140 or other biasing element positioned between the shelf 110 and a lowermost coupling mechanism 130. The spring 140 is configured to bias a position of the cannulated shaft 104 in a first direction extending away from the bone layer 26.

A rotary blade 150 is coupled to the lowermost end of the cannulated shaft 104. The rotary blade 150 includes a head 151 to which a plurality of spaced-apart blades 152 are coupled. The blades 152 can have any of various shapes and be any of various sizes. In the illustrated implementations, each blade 152 has a substantially tooth shape. Debris collection spaces are defined between adjacent blades 152. As pieces of the bone are cut away by the blades 152, the pieces collect within the debris collection spaces. As the pieces accumulate within the spaces, the pieces are forced upwardly within interior space of the sleeve 102 and may exit the sleeve via a plurality of debris ports 112 formed in the wall of the sleeve. In yet some embodiments, the planer 100 includes an injection port 114 formed in a side of the sleeve 102. A material source (e.g., a saline drip) may be coupled with the injection port to introduce a material into the cutting zone defined as the portion of the bone layer 26 being cut.

The cannulated shaft 104 includes an interior channel 120 extending coaxially along the shaft. The interior channel 120 is sized and shaped to receive a guide wire 122, which can be a standard K-wire commonly used in the art. The guide wire 122 includes a sharp end that is embeddable in the bone layer 26 at the site of the bone abnormality 27 to be removed. The position of the guide wire 122 determines the relative positions of the supplemental guide wires of the system 10 described below. Accordingly, the guide wire 122 acts as a primary or anchor guide wire. In certain implementations, the guide wires of the system 10 are embeddable into the bone layer 26 using the drill 30, other similar drill, or a K-wire driver specifically configured to drive K-wires. Once firmly embedded into the bone layer 26, the planer 100 is placed over and coupled to the primary guide wire 122 by extending the embedded guide wire through the channel 120 of the cannulated shaft 104. The serrated end 108 of the sleeve 102 is then embedded into the bone layer 26 about the abnormality 27. With the primary guide wire 122 extended through the shaft 104, the orientation of the planer 100 is aligned with the orientation of the primary guide wire 122. In this manner, the primary guide wire 122 properly aligns the planer 100 relative to the bone abnormality 27 to be removed.

After the planer 100 is placed over the primary guide wire 122, the bone planer 100 is operable to plane or remove the bone abnormality 27. With the rotary blade 150 rotatably driven by the drill 30, a user applies a downwardly directed force onto the drill to overcome the biasing force of the spring 140. As the biasing force of the spring 140 is overcome, the cannulated shaft 104 and rotary blade 150 is moved translationally toward the bone abnormality 27 until the blades 152 contact and cut through the abnormality to remove portions of the abnormality. The user continues to apply downwardly directed pressure to incrementally remove portions of the abnormality 27 until a sufficient amount of the abnormality (e.g., the entire abnormality) is removed. The planer 100 is then removed by sliding the planer upwardly out of engagement with the primary guide wire 122, which remains in place to accommodate proper positioning of the osteotomy guide 200.

Figure 4:
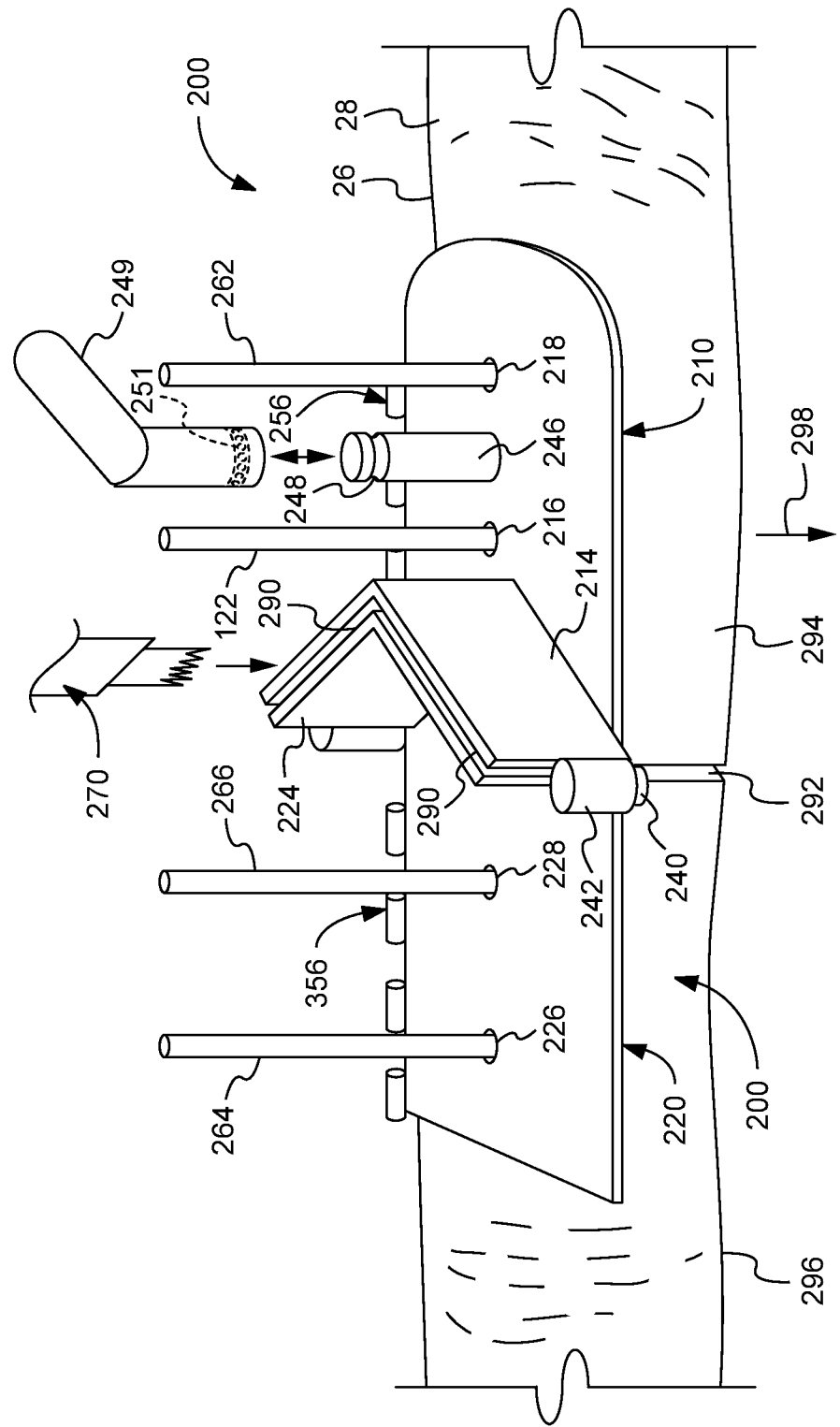
FIG. 4 is a top perspective view of the osteotomy guide of FIG. 3 being used in a bone osteotomy step of a bone realignment procedure.

Referring now to FIG. 3, the osteotomy guide 200 includes a distal portion 210 and a proximal portion 220. Generally, the distal and proximal portions 210, 220 of the guide 200 are coupled to each other and a bone in which an osteotomy will be performed. As shown in FIG. 4, when coupled to each other, the distal and proximal portions 210, 220 collectively define a cutting path 290 therebetween, which receives and guides a bone cutting instrument when making an osteotomy. The cutting path 290 ensures proper placement and quality of the osteotomy.

The distal portion 210 includes a base 212 from which a female upright 214 extends. The female upright 214 includes a proximally-facing surface 215 that defines a substantially V-shape. The distal portion 210 also includes apertures 216, 218 formed in the base 212 and configured to receive a respective K-wire embedded in a bone layer. The aperture 216 is positioned in the base 212 close to the female upright 214. In the illustrated embodiment, the aperture 216 is positioned just adjacent an apex of the female upright 214. The aperture 216 is configured to receive the primary guide wire 122 used in the placement of the planer 100. Therefore, the aperture 216 may be defined as a primary aperture. The aperture 218 is spaced distally away from the primary aperture 216. In the illustrated embodiment, the apertures 216, 218 are positioned in alignment along a medial line bisecting the distal portion 210. However, in other embodiments, the apertures 216, 218 can be positioned at any of various locations on the base 212.

A joystick stand 246 is coupled to and extends uprightly relative to the base 212 at a location between the apertures 216, 218. The joystick stand 246 includes a joystick retaining feature 248 formed in the stand and configured to mate with corresponding features 251 of a joystick 249 (see, e.g., FIG. 4). In the illustrated embodiment, the joystick retaining feature 248 is an annular recess and the features 251 of the joystick 249 are a plurality of radially movable balls, such that engagement between the balls and the recess facilitate a removably attachment between the joystick and the stand 246. In other embodiments, the joystick retaining feature 248 and corresponding features 251 on the joystick 249 can include other types of removable coupling arrangements. The distal portion 210 also includes a pair of posts 240 each positioned adjacent a respective lateral end of the female upright 214.

The proximal portion 220 includes a base 222 from which a male upright 224 extends. The male upright 224 includes a distally-facing surface 225 that defines a substantially V-shape corresponding with the V-shape of the female upright 214. The proximal portion 220 also includes apertures 226, 228 formed in the base 222 and configured to receive a respective K-wire embedded in a bone layer. The apertures 226, 228 are spaced apart and positioned in alignment along a medial line bisecting the proximal portion 220. However, in other embodiments, the apertures 226, 228 can be positioned at any of various locations on the base 222. The proximal portion 220 also includes a pair of receptacles 242 each positioned adjacent a respective lateral end of the male upright 224. Each receptacle 242 includes an open end 245 and a closed or capped end 247. Further each receptacle 242 defines a space 244 sized for receiving a respective one of the posts 240 through the open end 245. Generally, the receptacles 242 are configured to receive the posts 240 in slidable mating engagement. In other words, once received within the spaces 244, the posts 240 are able to slide relative to the receptacles 242. The closed ends 247 of the receptacles 242 act as stops to prevent slidable movement of the posts 240 beyond the closed ends.

In the illustrated embodiments, the uprights 214, 224 are female and male portions of a cutting guide. However, in other embodiments, the relative arrangement of the female and male uprights can be reversed. For example, the female upright 214 can be on the proximal portion 220 and the male upright 224 can be on the distal portion 210. Also, although the illustrated embodiments include uprights that form a substantially V-shaped or Chevron-shaped cutting path 290, in other embodiments, the uprights can be configured to form any of variously shaped and sized cutting paths as desired, such as Z-shaped, linear, arcuate, curved, and the like. Also, the uprights are substantially vertical to form a transverse cutting path 290. In other embodiments, however, the uprights can be angled to form angled cutting paths as desired.

In operation, the distal portion 210 is engaged with the primary guide wire 122 after the bone abnormality 27 is sufficiently planed and the planer 100 is removed. Engagement between the distal portion 210 and the guide wire 122 includes positioning the distal portion 210 such that the guide wire extends through the primary aperture 126 and sliding the distal portion along the guide wire until it rests on a lateral side 28 the bone 26 to be cut. After properly orienting the distal portion 210, a K-wire 262 is driven through the aperture 218 and into the bone 26. The two wires 122 and 262 maintain the position and orientation of the distal portion 210 during the osteotomy and alignment procedures. The proximal portion 220 is then positioned relative to the distal portion 210 such that the receptacles 242 matingly receive the posts 240 within the spaces 244 as indicated by directional arrow 261. Engagement between the receptacles 242 and posts 240 at least partially maintains the position and orientation of the proximal portion 210 relative to the bone 26 and distal portion during the osteotomy and alignment procedures. To further maintain the position and orientation of the proximal portion 210, respective K-wires 264, 266 are driven through the apertures 226, 228 and into the bone 26. The joystick 249 can then be removably coupled to the stand 246.

With the proximal portion 220 coupled to the distal portion 210, the cutting path 290 is defined between the female and male uprights 214, 224. The uprights 214, 224 have a height sufficient to allow a cutting blade or saw 272 of a cutting tool 270 to pass through the cutting path 290 and into the bone 26 to form a cut 292 in the bone. Additionally, the height of the uprights 214, 224 maintains the orientation of the cutting blade 272 throughout the cutting process such that uneven or non-uniform cuts are avoided. Further, the thickness of the cutting path 290 (i.e., the space defined between the uprights 214, 224) is sufficient to allow the cutting blade 272 to pass through the path, but small enough to prevent the blade 272 from tilting or swaying during the cutting process. After the cutting blade 272 cuts the desired osteotomy 292 through the bone 26, which corresponds with the shape of the cutting path 290 (e.g., a Chevron shape), the bone 26 is bisected into a distal fragment or capital fragment 294 and a proximal fragment 296.

Figure 5:
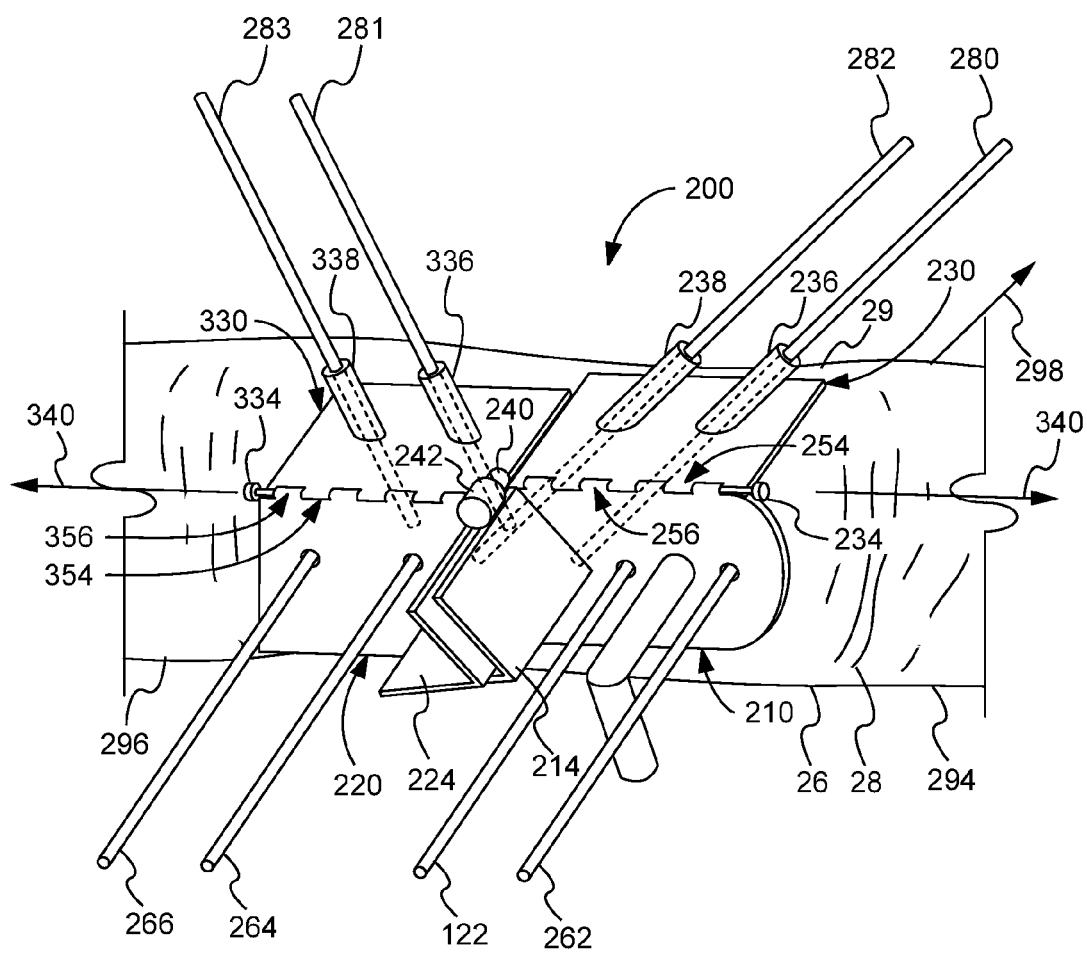
FIG. 5 is a side perspective view of the osteotomy guide of FIG. 3 being used in a bone segment moving step of a bone realignment procedure.

Referring to FIG. 5, with the capital fragment 294 severed from the proximal fragment 296, a user may then realign the capital fragment by grasping the joystick 249 and manually moving the capital fragment relative to the proximal fragment in a lateral direction indicated by directional arrow 298. As the capital fragment 294 is moved or shifted laterally, the distal portion 210 of the guide 200 also moves laterally relative to the proximal portion 220 of the guide. The lateral movement between the distal and proximal portions 210, 220 is facilitated by sliding engagement between the posts 240 and receptacles 242. In other words, as the distal portion 210 moves laterally relative to the proximal portion 220, the posts 240 slide at least partially out of the receptacles 242 as shown in FIG. 5. However, throughout the lateral movement of the capital fragment 294 and distal portion 210, at least a portion of the posts 240 remains engaged with the receptacles 242 such that the orientation and axial position of the capital fragment relative to the proximal fragment is maintained.

Once the capital fragment 294 is realigned into a new desired position relative to the proximal fragment 296, the capital fragment should be secured in place by passing one or more anchor fasteners (e.g., set screw) through the capital segment and into the proximal segment. To facilitate proper positioning and securing of the anchor fasteners, the guide 100 includes anchor fastener alignment features or panels or doors 230, 330 that are removably coupled to the distal and proximal portions 210, 220, respectively, of the guide. Referring to FIGS. 3-5, the fastener alignment features 230, 330 include a base 232, 332 from which respective alignment sleeves 236, 238, 336, 338 extend. The placement of the sleeves 236, 238 on the base 232 correspond with the location of respective apertures 250, 252 formed in the base such that the sleeves 236, 238 are aligned with the apertures 250, 252, respectively. The alignment sleeves 336, 338 are similar configured but are angled proximally, as opposed to distally as with the alignment sleeves 236, 238. The fastener alignment features 230, 330 also include respective first hinge portions 254, 354 including a plurality of eyelets configured to receive a respective removable pin 233, 333. The pins 233, 333 include knobs 234, 334 to facilitate gripping and removing the pins.

The fastener alignment features 230, 330 are coupled to the distal and proximal portions 210, 220 such that the fastener alignment features are placed over a dorsal side 29 of the bone 26. More specifically, the bases 232, 332 of the fastener alignment features extend substantially transversely relative to the bases 212, 222 of the distal and proximal portions 210, 220, respectively. The alignment features 230, 330 are coupled to the distal and proximal portions 210, 220 via mating second hinge portions 256, 356 forming part of the distal and proximal portions 210, 220, respectively. The second hinge portions 256, 356 each includes a plurality of eyelets configured to receive the removable pins 233, 333, respectively, as well as to be positioned in alignment between the eyelets of the first hinge portions 254, 354 of the respective alignment features 230, 330. When the respective first and second hinge portions 254, 256, 354, 356 are aligned, the pins 233, 333 are extended through the respective eyelets to couple in pivotal engagement the distal and proximal portions 210, 220 and the fastener alignment features 230, 330, respectively.

Once the alignment feature 230 is removably coupled to the distal portion 210 of the guide 200, a pair of K-wires 280, 282 are driven through the respective alignment sleeves 236, 238, through the capital fragment 294, and into the proximal fragment 296. Similarly, once the alignment feature 330 is removably coupled to the proximal portion 220 of the guide 200, a pair of K-wires 281, 283 are driven through the respective alignment sleeves 336, 338, through the proximal fragment 296, and into the capital fragment 294. When placed, the K-wires 280, 282, 281, 283 at least temporarily maintain the placement of the realigned capital fragment 394 and the proximal fragment 296. As shown, the K-wires 280, 282 penetrate the capital and proximal fragments in a distal-to-proximal direction. In contrast, the K-wires 281, 283 penetrate the capital and proximal fragments in a proximal-to-distal direction. Securing the capital and proximal fragments from both directions provides certain advantages. However, in certain embodiments, only one of the alignment features for securing the capital and proximal fragments together in a single direction is required.

The alignment sleeves 236, 238, 336, 338 act to guide and align the K-wires 280, 282, 281, 283 into a desired orientation corresponding with the placement of anchor or set screws. Accordingly, the alignment sleeves 236, 238, 336, 338 may necessarily be angled in order for the K-wires 280, 282, 281, 283 to be driven through both the capital and proximal fragments. Although each alignment feature 230, 330 of the illustrated embodiments includes two alignment sleeves each at a specific angle with respect to the bases, in other embodiments, each alignment feature can include one or more than two alignment sleeves each at any of various angles as desired.

After driving the K-wires 280, 282, 281, 283 into the capital and proximal fragments 294, 296, the alignment features 230, 333 should be removed in preparation of more permanently securing the capital and proximal fragments with set screws. The alignment features 230, 330 are removable from the distal and proximal portions 210, 220 of the guide 200 by slidably removing the pins 233, 333 out of engagement with the first and second hinge portions 254, 256, 354, 356, as indicated by directional arrows 340, and then sliding the alignment features away from the bone 26 along the K-wires 280, 282, 281, 283, respectively, until they are is completely removed from the system 10. Then, following, or before, removal of the K-wires 122, 262, 264, 266, the distal and proximal portions 210, 220 of the guide 200 can be removed. Although not shown, respective cannulated set screws are then placed over the K-wires 280, 282, 281, 283 which act as guides for driving the set screws into the capital and proximal fragments 294, 296 at a desired angle and direction. Further trimming of sharp joints left over from the osteotomy can then be performed as necessary.

Figure 6:
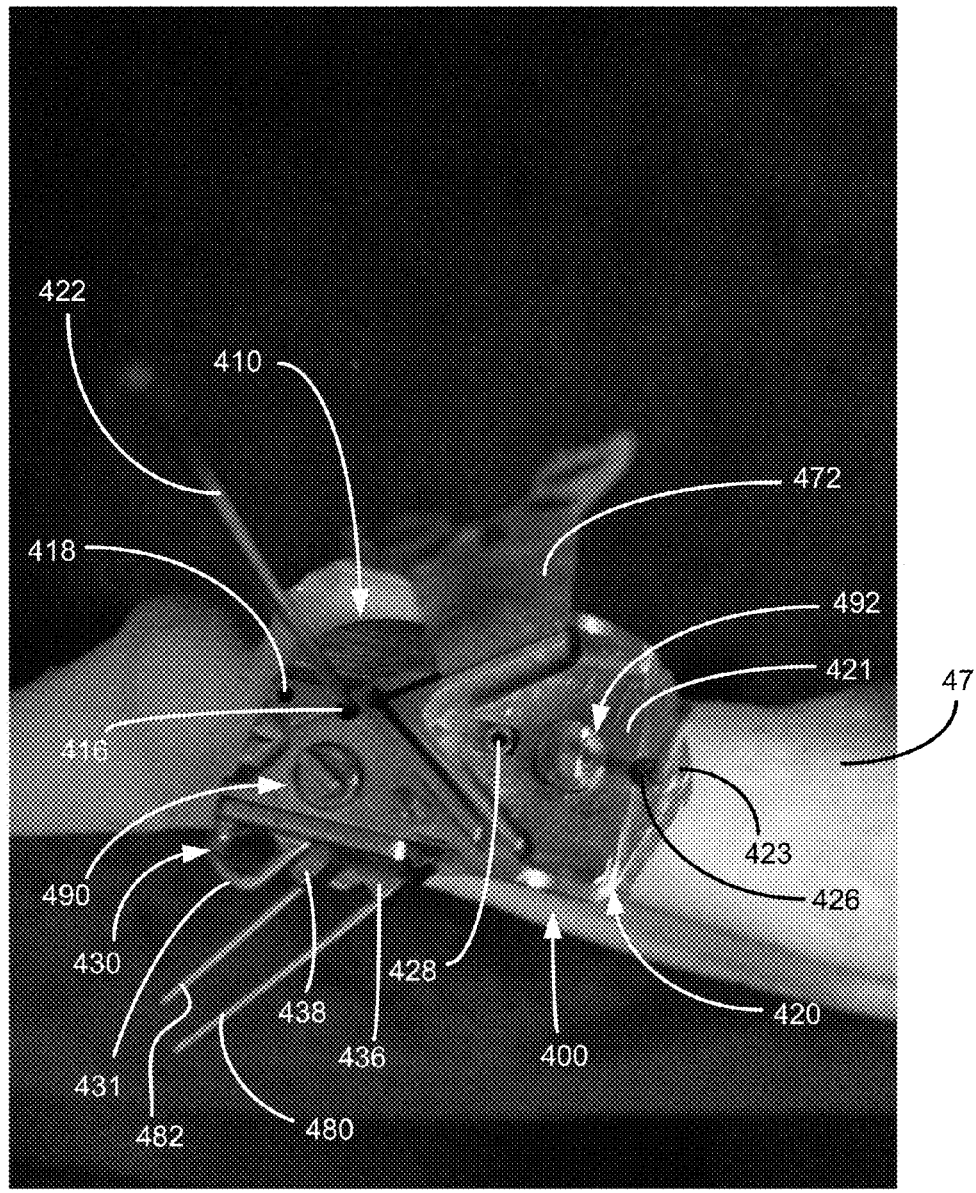
FIG. 6 is a top perspective view of an osteotomy guide according to one embodiment used in a bone osteotomy step of a bone realignment procedure.
Figure 7:
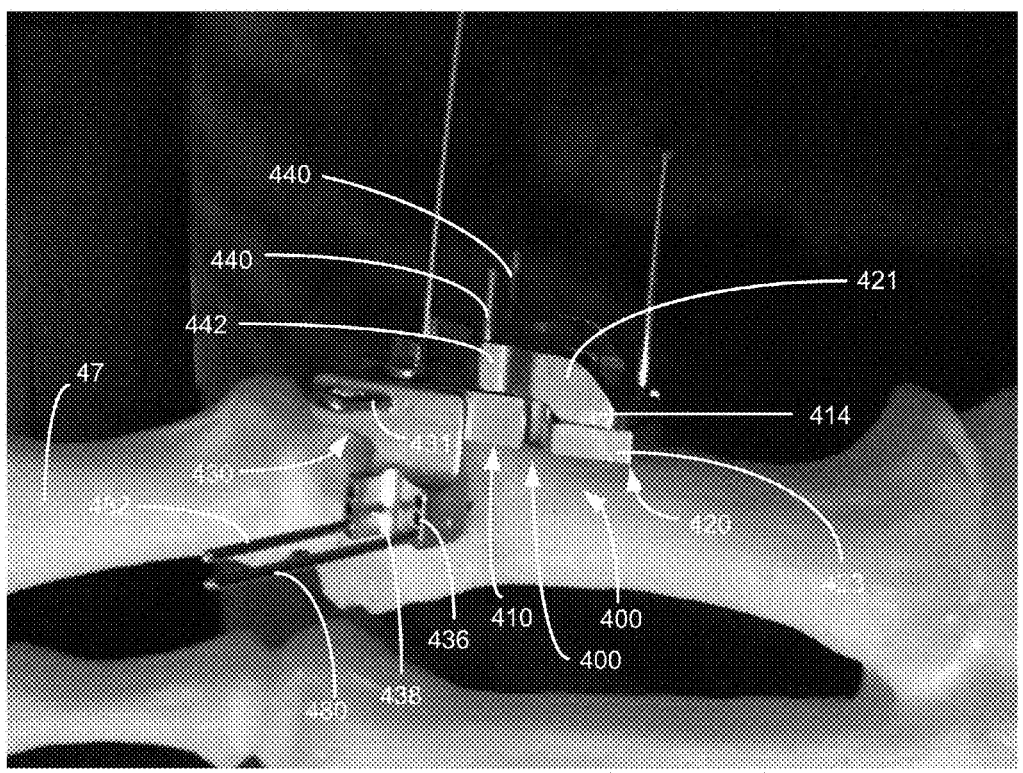
FIG. 7 is perspective side view of the osteotomy guide of FIG. 6.
Figure 8:
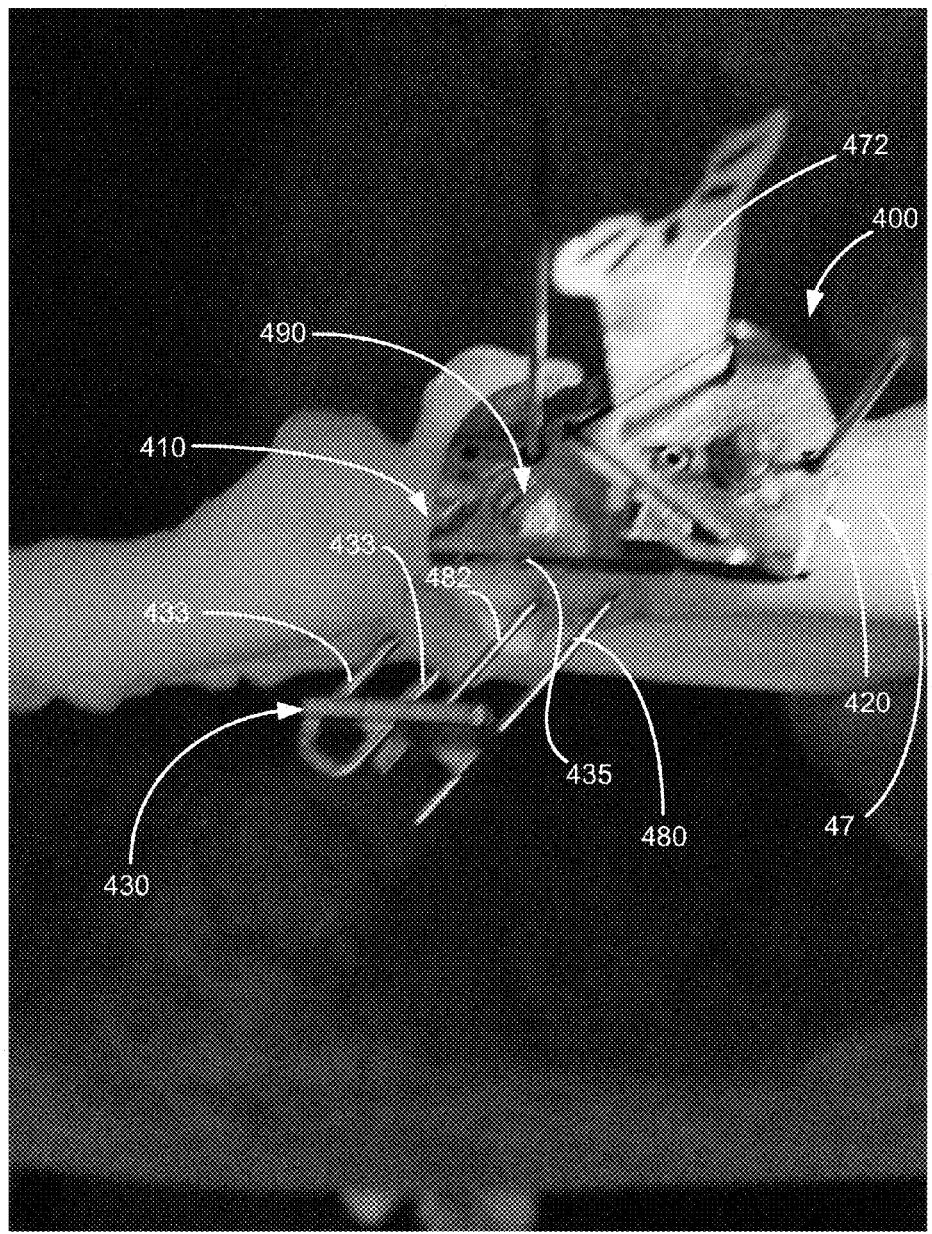
FIG. 8 is a top perspective view of the osteotomy guide of FIG. 6 shown with a removable fastener alignment door being removed from the guide according to one embodiment.

According to another embodiment shown in FIGS. 6-8, an osteotomy guide 400 can be used to facilitate an osteotomy and realignment of a bone. The osteotomy guide 400 is similar to the osteotomy guide 200 described above, with like numbers referring to like elements. For example, the osteotomy guide 400 includes a distal portion 410 and proximal portion 420 that interact with each other in a manner similar to the distal and proximal portions 210, 220 of the osteotomy guide 200 to define a cutting path between two uprights. Moreover, like the slidable engagement between the posts 240 and receptacles 242 of the osteotomy guide 200, the distal portion 410 is laterally slidable relative to the proximal portion 420 via slidable engagement between rods 440 fixed to the distal portion and sleeves 442 fixed to the proximal portion. However, the osteotomy guide 400 has certain differences compared to the osteotomy guide 200 as will be described in more detail below.

Similar to the fastener alignment feature 330 of the osteotomy guide 200, the osteotomy guide 400 includes a fastener alignment feature or panel or door 430 that is releasably coupled to the distal portion 410. However, the door 430 is releasably coupled to the distal portion 410 in a manner different than the osteotomy guide 200. More specifically, the door 430 is not pivotally coupled to the distal portion 410 via a hinged connection. Rather, the distal portion 410 includes channels 435 that receive respective prongs 433 of the door 430 to couple the door to the distal portion. When coupled, the door 430 extends substantially perpendicular relative to the distal portion 410, but can extend at any of various angles in other embodiments. The distal portion 410 includes a quick release mechanism 490 configured to selectively lock the prongs 433 in place within the channels 435 to lock the door 430 to the distal portion 410, and selectively unlock the prongs to allow the prongs to be pulled out of the channels for removing the door from the distal portion (see, e.g., FIG. 8). The quick release mechanism 490 includes an adjustable knob that is accessible to a user. The knob can be actuated (e.g., rotated or slid) to lock the door 430 to and unlock the door from the distal portion 410. The quick release mechanism 490 can be configured to incorporate any of various quick release mechanism devices and techniques known in the art.

To facilitate removal of the door 430 along the guide pins 480, 482, the prongs 433 are parallel to the alignment sleeves 436, 438 to avoid binding. Also, as shown in FIG. 7, the door 430 includes at least two sets of multiple alignment sleeves 436, 438 to accommodate different fixation positions of the guide wires 480, 482, or to accommodate multiple guide wires in multiple alignment sleeves of one set. The door 430 may also include a handle 431 to accommodate grasping the handle for installing the door onto the distal portion 410 prior to setting the guide wires 490, 482 in the bone and removing the door from the distal portion after the guide wires are set in the bone.

After cutting the bone using the bone blade 472, and laterally shifting the distal or capital fragment of the bone into a realigned position relative to a proximal fragment, it may be desirable to compress the realigned bone fragments together to facilitate proper healing before the guide wires 480, 482 are set through the sleeves 436, 438 and into the bone 47. Accordingly, the proximal portion 420 is configured to accommodate compression of the bone fragments before fixing the realigned bone fragments together. The proximal portion 420 includes an upper section 421 and lower section 423 that is slidable relative to the upper section. The upper section 421 includes the sleeves 442. Accordingly, when the sleeves 442 are slidably engaged with the rods 440 of the distal portion 430, the upper section 420 of the proximal portion 420 is axially (e.g., a direction perpendicular to the longitudinal direction of the rods 440) fixed relative to the distal portion 430. In contrast, the lower section 423 includes the upright that defines the cut path between itself and the upright of the distal portion 430.

The lower section 423 is movable (e.g., slidable) relative to the upper section 421, and thus is movable relative to the distal portion 430 even when the sleeves 442 are slidably engaged with the rods 440 of the distal portion 430. Therefore, after the blade 472 is removed, the lower section 423 can be slid relative to the upper section toward the distal portion 430 to decrease the gap or space between the adjacent uprights defining the cut path. Also, because the lower section 423 includes the aperture 426 through which the guide pin 466 extends into the bone, and the distal portion 430 includes the aperture 416 through which the guide pin 422 extends into the bone, the lower section 423 is fixed relative to the proximal bone fragment and the distal portion is fixed relative to the distal bone fragment. Accordingly, when the lower section 423 is slid relative to the distal portion 430, the distal bone fragment is moved closer to (e.g., compressed against) the proximal bone fragment to close the gap between the fragments to facilitate healing. Sliding the lower section 423 relative to the upper section 421 to compress the fragments together can be facilitated by actuation (e.g., rotation) of the knob 492. The knob 492 may be coupled to a cam mechanism that forces the lower section 423 to slide relative to the upper section 421 as the knob is rotated.

Reference throughout this specification to "one embodiment," "an embodiment," or similar language means that a particular feature, structure, or characteristic described in connection with the embodiment is included in at least one embodiment of the present invention. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

Reference throughout this specification to features, advantages, or similar language does not imply that all of the features and advantages that may be realized with the subject matter of the present disclosure should be or are in any single embodiment or implementation of the subject matter. Rather, language referring to the features and advantages is understood to mean that a specific feature, advantage, or characteristic described in connection with an embodiment is included in at least one embodiment of the subject matter of the present disclosure. Discussion of the features and advantages, and similar language, throughout this specification may, but do not necessarily, refer to the same embodiment or implementation.

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings.

The subject matter of the present application may be embodied in other specific forms without departing from its spirit or essential characteristics. The described embodiments are to be considered in all respects only as illustrative and not restrictive. The scope of the subject matter is, therefore, indicated by the appended claims rather than by the foregoing description. All changes which come within the meaning and range of equivalency of the claims are to be embraced within their scope.

What is claimed is:

1. An osteotomy guide, comprising:
 a distal portion comprising a first upright defining a first cut guide surface; and
 a proximal portion comprising a second upright defining a second cut guide surface;
 wherein the distal portion is laterally slidably coupleable to the proximal portion, and wherein when the distal portion is laterally slidably coupled to the proximal portion a cut path for receiving a cutting blade is defined between the first and second cut guide surfaces; and
 wherein the distal portion is slidably coupleable to the proximal portion via a coupling mechanism, wherein when slidably coupling the distal and proximal portions, the coupling mechanism allows movement of the distal portion relative to the proximal portion in a first direction and prevents movement of the distal portion relative to the proximal portion in a second direction perpendicular to the first direction.

2. The osteotomy guide of claim 1, wherein the distal portion comprises at least one aperture for receiving a guide wire, and the proximal portion comprises at least one aperture for receiving a guide wire.

3. The osteotomy guide of claim 1, wherein the proximal portion comprises first and second sections, the first section being axially fixedly coupled to the distal portion and the second section being axially movable relative to the distal portion, wherein the second upright is fixedly attached to the second section.

4. The osteotomy guide of claim 1, further comprising at least one distal panel removably coupleable to the distal portion.

5. The osteotomy guide of claim 4, wherein the at least one distal panel comprises at least one guide sleeve configured to receive a guide wire.

6. The osteotomy guide of claim 1, wherein the cut path has a V-shape.

7. A method for cutting and aligning bone, comprising:
 securing a proximal portion of an osteotomy guide to a bone to be cut, the proximal portion defining a first cut guide surface;
 slidably coupling a distal portion of the osteotomy guide to the proximal portion, the distal portion defining a second cut guide surface, wherein when the distal portion is slidably coupled to the proximal portion, a cut path is defined between the first and second cut guide surfaces;

passing a cutting blade through the cut path and into the bone to cut the bone into a first segment and second segment;
slidably moving the proximal portion relative to the distal portion to move the first segment of the bone into a new position relative to the second segment of the bone; and
fixing the first segment of the bone in the new position relative to the second segment of the bone.

\* \* \* \* \*